US00PP12781P2

(12) United States Plant Patent
Kanno

(10) Patent No.: US PP12,781 P2
(45) Date of Patent: Jul. 16, 2002

(54) OSTEOSPERMUM PLANT NAMED 'KAKEGAWA AU6'

(75) Inventor: Masao Kanno, Chigasaki (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/657,536

(22) Filed: Sep. 8, 2000

(51) Int. Cl.[7] ..... A01H 5/00

(52) U.S. Cl. ..... Plt./360

(58) Field of Search ..... Plt./360

*Primary Examiner*—Bruce R. Campell
*Assistant Examiner*—Annette Para
(74) *Attorney, Agent, or Firm*—Rothwell, Figg, Ernst & Manbeck

(57) ABSTRACT

The present invention relates to a new and distinct variety of *Osteospermum fruticosum* (L.) Norl plant named 'Kakegawa AU6'. This new plant has a suitable form for pot culture and also possesses large yellow flowers that stay open into the evening hours or under low light conditions.

1 Drawing Sheet

BACKGROUND OF THE INVENTION

The present invention relates to a new and distinct variety of the Compositae family. The new variety, a member of the species *Osteospermum fruticosum* (L.) Norl., named 'Kakegawa AU6'. This species is one of several species of Osteospermum that are commonly referred to as Cape Daisy.

The new variety originated as a first generation hybrid seedling following four generations of random intercrossing between population selections. All crosses were done at the Sakata Seed Corporation, Chogo Research Station in Chogo Prefecture, Japan. The objective of this breeding program was to develop plants with suitable form for pot culture that also possessed large flowers that would stay open into the evening hours. The flowers of *Osteospermum fruticosum* (L.) Norl. usually close under low light conditions, such as in the evening.

In 1989, the *Osteospermum fruticosum* (L.) Norl. breeding population was initiated that produced the female parent of the initial cross of this variety. Five generations of plant selection and intercrossing occurred until breeding line 573 was selected in 1994. Plant selection was made for the yellow petal color and flowers that remained open in the afternoon or evening.

In 1991, the *Osteospermum fruticosum* (L.) Norl. breeding population was started that produced the male parent of the initial cross of this variety. Three generations of plant selection and intercrossing occurred until breeding line 601 was selected in 1994. Plant selection was made for yellow petal color and flowers that remained open in the afternoon or evening.

In 1994, line 573 was crossed with line 601. The $F_1$ seed was sown that Fall and in Spring of 1995, line 790 was selected. Line 790 was selected because of its unique white petals with yellow tips and the characteristic of keeping its flowers open late into the afternoon. Line 790 was asexually reproduced and further evaluated before being renamed 'Kakegawa AU6' in 1996. Further evaluation by the inventor during 1997 and 1998 demonstrated that the new variety's characteristics were firmly fixed and stable. Since this time the new variety has been trialed and vegetatively propagated at the Sakata Seed Corporation facility in Salinas, Calif. The new variety has been stable and fixed in this environment also.

The new variety has been observed under greenhouse and outdoor conditions in California and Japan. The phenotype of the new plant may vary somewhat with variations in temperature, day length, light intensity or soil media conditions. The observations noted below have been made using multiple 8 month old plants grown in Salinas, Calif. under the following conditions. Shoot tips were rooted in soil plug trays in August. After developing a root ball the plants were transplanted into six-inch diameter pots and grown outdoors through the winter to provide vernalization for flowering. In December, buds were pinched off to promote branching. Winter night temperatures averaged 40 to 50 degrees Fahrenheit. By May of the following year the plants were in full bloom. Average summer daytime temperatures in Salinas range from 60 to 75 degrees Fahrenheit depending on the month and the amount of coastal marine layer cloud cover.

BRIEF DESCRIPTION OF THE PHOTOGRAPHS

The accompanying color photographs illustrate the appearance the new variety, 'Kakegawa AU6'. The colors are represented as true as possible using conventional photographic procedures.

DETAILED DESCRIPTION OF THE NEW VARIETY

Figure 1:
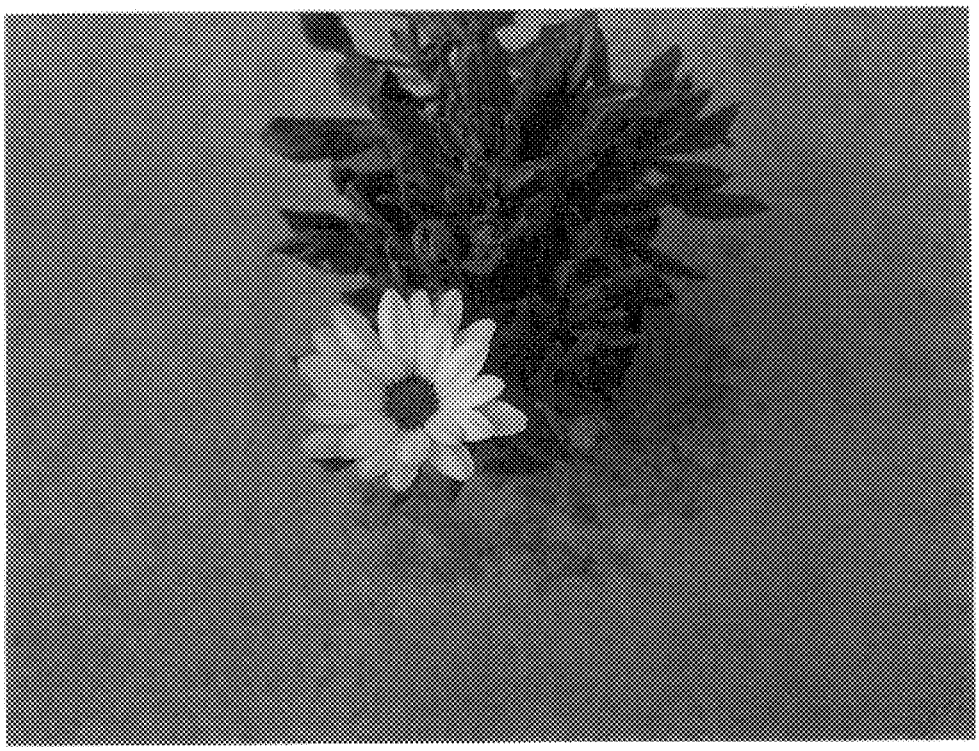
FIG. 1 is a close-up view of a single, young bloom illustrating the ray floret color of young blooms being a solid yellow color.
Figure 2:
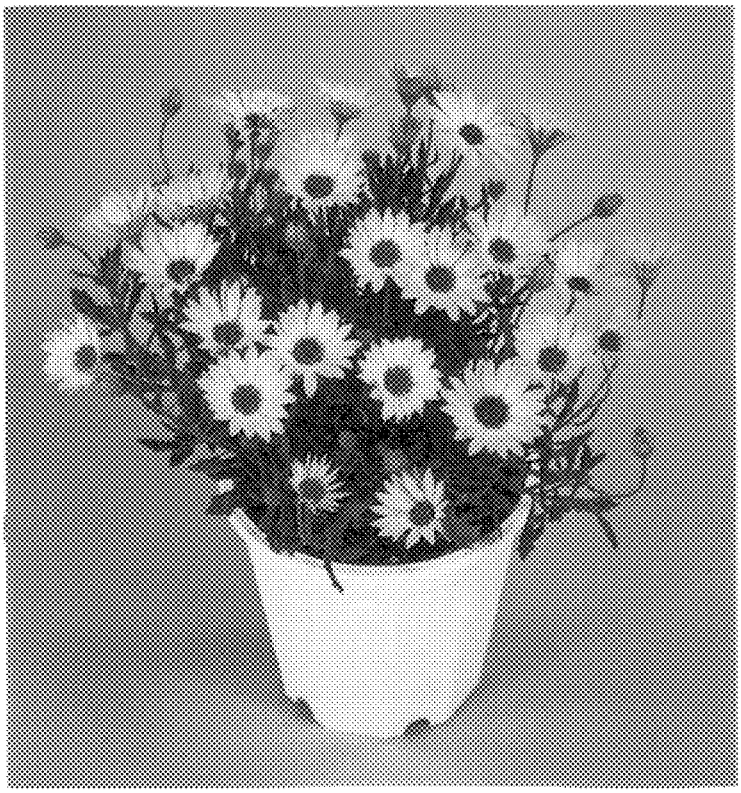
FIG. 2 is a view of the entire plant showing its form in pot culture when in full bloom.

The following traits and characteristics describe the new variety. Color references are made to The Royal Horticultural Society Colour Chart (R.H.S.), published by The Royal Horticultural Society of London, England, except where general terms of ordinary significance are used.

Classification:

*Family.*—Compositae (Asteraceae).

*Genus and species.*—*Osteospermum fruticosum* (L.) Norl.

*Common names.*—African Daisy, Cape Daisy, Freeway Daisy.
*Cultivar name.*—'Kakegawa AU6'.

Parentage:
*Female parent.*—Line 573 (not patented).
*Male parent.*—Line 601 (not patented).

Growth:
*Habit.*—Vigorous, well branched.
*Life cycle.*—Perennial.

Plant description:
*Height.*—38 cm to 42 cm.
*Width.*—40 cm to 50 cm.
*Form.*—Upright, conical-like.
*Lastingness of individual florescences.*—7 days.

Stems:
*Stem color.*—RHS 144A (yellow-green).
*Stem description.*—Strong, erect, herbaceous, glabrous.
*Stem diameter.*—3 mm to 4 mm.
*Internode length.*—0.8 cm to 1.0 cm.

Leaves:
*Leaf arrangement.*—Alternate; sessile.
*Leaf apex.*—Mucronate.
*Leaf base.*—Oblique.
*Leaf color.*—Upper surface RHS 137A (green); lower surface RHS 137D (green).
*Leaf edge.*—Slightly serrated.
*Leaf shape.*—Lanceolate.
*Leaf venation.*—Pinnate.

Flowers:
*Phyllaries.*—Arrangement — symmetrical; length 13 mm; width 1.5 mm; shape linear; apex acute; margin entire; texture pubescent; upper color RHS 137D (green); lower color RHS 138C (green).
*Corolla.*—Free.
*Flower diameter.*—8.1 cm.
*Flowering habit.*—Determinate.
*Fragrance.*—None.
*Inflorescence type.*—Solitary on terminal peduncles.
*Ovary.*—Inferior.
*Peduncle.*—Texture pubescent; length 6–9 cm; diameter 0.2 cm; color RHS 143C (green).
*Bud.*—Shape round, pointed at the top; length 1.3 cm; width 0.8 cm; color RHS 143C (green).
*Ray floret color.*—Dorsal surface of ray florets are solid RHS 94 (yellow) when young then transition to RHS 8C (yellow) with RHS 78B (purple) blush; ventral surface of ray florets is RHS 16B (yellow-orange) with RHS 166B (brown) streaks; disk florets are RHS 16C (yellow-orange).
*Ray floret shape.*—Spatulate; apex obtuse; margin entire.
*Ray floret size.*—3.7 cm in length; 0.8 cm in width.
*Ray floret number.*—16.
*Disc floret shape.*—Tubular.
*Disc floret size.*—5.0×0.7 mm.
*Disc floret number.*—55 per head.
*Propagation to bloom.*—18 to 20 weeks when rooted vegetative cuttings are transferred to a six-inch diameter pot in late Fall and given several weeks of below 50 degree Fahrenheit temperature prior to increasingly warmer spring weather.

Reproductive organ:
*Stigma.*—RHS N82A (purple-violet).
*Style.*—RHS 155D (white).
*Anther.*—RHS N77A (purple).
*Filament.*—RHS 4D (yellow).
*Fruit and seed.*—Not produced.

DISEASE AND INSECT RESISTANCE

No known susceptibility to diseases or insects have been observed to date.

COMPARISON WITH OTHER KNOW VARIETIES

The closest known variety to 'Kakegawa AU6' is the variety 'Brightside', a plant described and illustrated in U.S. Plant Pat. No. 10,596. The following table compares the differences that distinguish the new variety from the similar variety 'Brightside'.

| Characteristic | 'Kakegawa AU6' | 'Brightside' |
|---|---|---|
| Disk florets | RHS 16C (yellow-orange) | RHS 90C (violet-blue) |
| Flower diameter (cm) | 8.1 | 5.7 |
| Growth form | Upright, conical-like | Upright, broad |
| Leaf width (cm) | 0.89 | 1.45 |
| Ray floret color (dorsal) | RHS 8C (yellow) with RHS 78B (purple) blush at base | Pure white |
| Ray floret color (ventral) | RHS 16B (yellow-orange) with RHS 166B brown streaks | RHS 90B (violet-blue) |

I claim:

1. A new and distinct plant of the Compositae family, *Osteospermum fruticosum* (L.) Norl., herein referred to by the name 'Kakegawa AU6', as illustrated and described.

* * * * *